(12) United States Patent
Meixner et al.

(10) Patent No.: US 10,286,127 B2
(45) Date of Patent: *May 14, 2019

(54) POUCH-SHAPED WOUND DRESSING SYSTEM

(71) Applicant: 3M INNOVATIVE PROPERTIES COMPANY, St. Paul, MN (US)

(72) Inventors: Carsten Meixner, Hückeswagen (DE); Haythem Korbi, Wuppertal (DE)

(73) Assignee: 3M Innovative Properties Company, St. Paul, MN (US)

(*) Notice: Subject to any disclaimer, the term of this patent is extended or adjusted under 35 U.S.C. 154(b) by 303 days.

This patent is subject to a terminal disclaimer.

(21) Appl. No.: 15/036,142

(22) PCT Filed: Nov. 12, 2014

(86) PCT No.: PCT/EP2014/074311
§ 371 (c)(1),
(2) Date: May 12, 2016

(87) PCT Pub. No.: WO2015/071279
PCT Pub. Date: May 21, 2015

(65) Prior Publication Data
US 2016/0279306 A1 Sep. 29, 2016

(30) Foreign Application Priority Data

Nov. 13, 2013 (EP) .................................... 13192646

(51) Int. Cl.
*A61M 1/00* (2006.01)
*A61F 13/00* (2006.01)
*A61M 35/00* (2006.01)

(52) U.S. Cl.
CPC ..... *A61M 1/0084* (2013.01); *A61F 13/00017* (2013.01); *A61F 13/00029* (2013.01);
(Continued)

(58) Field of Classification Search
CPC .............. A61M 1/0084; A61M 1/0037; A61M 1/0088; A61M 35/00; A61F 13/00017;
(Continued)

(56) References Cited

U.S. PATENT DOCUMENTS 4,382,441 A * 5/1983 Svedman .......... A61F 13/00068
604/114
5,141,031 A 8/1992 Baurmeister
(Continued)

FOREIGN PATENT DOCUMENTS

DE 28 33 493 2/1980
DE 38 39 567 6/1990
(Continued)

OTHER PUBLICATIONS

International Search Report for PCT International Application No. PCT/EP2014/074311 dated Dec. 11, 2014, 4 pages.
(Continued)

*Primary Examiner* — Tatyana Zalukaeva
*Assistant Examiner* — Gabriella E Burnette
(74) *Attorney, Agent, or Firm* — Scott A. Baum

(57) ABSTRACT

A wound dressing system having a capillary membrane system arranged in a pouch-shaped wound dressing that is closed at its outer edge. The pouch-shaped wound dressing having an upper face, a lower face, and an interior formed from planar materials with the lower face permeable to fluids. The capillary membrane system is arranged into the interior of the pouch-shaped wound dressing.

12 Claims, 2 Drawing Sheets

Figure 1:
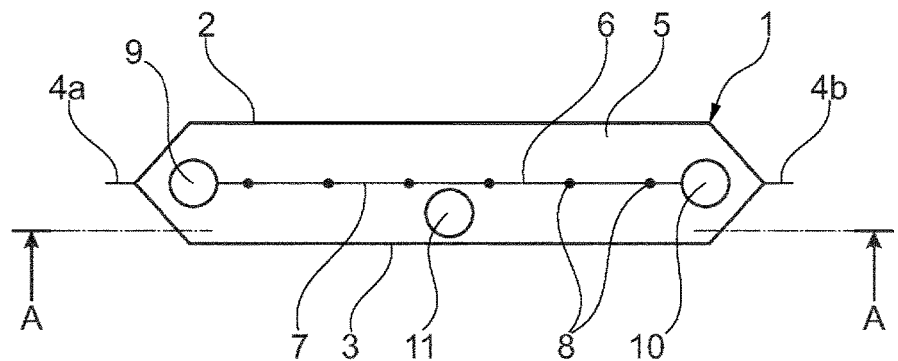

(52) U.S. Cl.
CPC ..... *A61F 13/00068* (2013.01); *A61M 1/0037* (2013.01); *A61M 1/0088* (2013.01); *A61F 13/00012* (2013.01); *A61F 13/00021* (2013.01); *A61F 13/00042* (2013.01); *A61F 2013/0017* (2013.01); *A61F 2013/00548* (2013.01); *A61M 35/00* (2013.01)

(58) Field of Classification Search
CPC .......... A61F 13/00029; A61F 13/00068; A61F 13/00012; A61F 13/00021; A61F 13/00042; A61F 2013/0017; A61F 2013/00548
See application file for complete search history.

(56) References Cited

U.S. PATENT DOCUMENTS

| | | | |
|---|---|---|---|
| 5,549,584 | A | 8/1996 | Gross |
| 6,410,307 | B1 | 6/2002 | Glockner |
| 6,497,752 | B1 | 12/2002 | Kessler |
| 9,321,013 | B2 * | 4/2016 | Bornemann ........ A61M 1/0084 |
| 9,907,708 | B2 * | 3/2018 | Riesinger .......... A61F 13/00017 |
| 10,039,673 | B2 * | 8/2018 | Mumby ............ A61F 13/00059 |
| 2009/0191631 | A1 | 7/2009 | Bornemann |
| 2009/0196855 | A1 * | 8/2009 | Bornemann ........ A61M 1/0084 424/93.7 |
| 2012/0215193 | A1 * | 8/2012 | Siniaguine .......... A61F 13/0206 604/368 |
| 2013/0023842 | A1 | 1/2013 | Song |

FOREIGN PATENT DOCUMENTS

| | | |
|---|---|---|
| DE | 43 08 850 | 9/1994 |
| DE | 102 21 565 | 12/2003 |
| DE | 102009039868 | 3/2011 |
| EP | 0 299 381 | 1/1989 |
| WO | WO 2007/116072 | 10/2007 |
| WO | WO 2008/106515 | 9/2008 |
| WO | WO 2010/037092 | 4/2010 |
| WO | WO 2013/066426 | 5/2013 |

OTHER PUBLICATIONS

OA for U.S. Appl. No. 16/036,195 dated Jun. 14, 2018 (15 pages).
Notice of Allowance for U.S. Appl. No. 15/036,195 dated Dec. 26, 2018 (9 pages).

* cited by examiner

POUCH-SHAPED WOUND DRESSING SYSTEM

CROSS REFERENCE TO RELATED APPLICATIONS

This application is a national stage filing under 35 U.S.C. § 371 of PCT/EP2014/074311, filed Nov. 12, 2014, which claims the benefit of European Patent Application No. 13192646.1, filed Nov. 13, 2013, the disclosures of which are incorporated by reference in their entirety herein.

The invention relates to a wound dressing system comprising at least one mat-like capillary membrane system for introduction into a wound or for applying on top of a skin wound and underneath a wound bandage.

The aim of modern wound care is to create a moist environment for wound care which promotes the processes taking place during healing. Depending on the healing phase, modern active wound dressings must therefore be capable of keeping the wound moist and/or conveying away large amounts of exudate. In wound care, it is important to provide for an improved liquid/material exchange, for introducing factors/medications into the wound and/or for improving the removal of liquid/secretion and/or material from the wound. Applications include the use of such wound dressing systems in a soft tissue wound, in an abdominal wound and on a skin wound.

A method and a device for removing secretions or exudate from wounds is commercially known as V.A.C.® Therapy System (from KCI, USA). This system provides for an alternating introduction of liquid into the wound and a subsequent, hence also alternating and thus non-continuous, removal of liquid from the wound. A foam material introduced into the wound, which exerts forces on the wound at negative pressure, is intended to promote wound healing in this system.

DE 10 2003 042 732 describes a capillary membrane system for wound care in which the wound is perfused and supplied via a hollow membrane arrangement consisting of up to 1000 hollow fibers having at least one common supply line and at least one common discharge line in the context of perfusing a capillary bed, and which should make possible perfusion with an antibiotic and growth factor. This should make possible uniform material distribution under continuous perfusion, even when a moderate vacuum is created. In order to improve treatment outcome, in parallel with wound care, the device should moreover be capable of introducing cells.

Although progress in wound care has already been made with the capillary membrane system described in DE 10 2003 042 732, there is a continued need for improved wound care systems with which the processes necessary for wound care can be carried out, such as flushing and disinfecting without removing bandages, which, if necessary, make possible nutrient supply, temperature control, oxygenation, pH regulation, electrolyte replacement and/or detoxification or even a supply of growth factor or antibiotics, and which facilitate easy and safe handling.

The problem of the present invention is to provide such a wound care system.

The problem is solved by a wound dressing system to be introduced into a wound, which comprises at least one planar capillary membrane system and which is characterized in that the at least one planar capillary membrane system is arranged in a pouch-shaped wound dressing which is closed at its outer edge and which has an upper face, a lower face and a interior of the pouch, wherein the lower face and the upper face are each formed from a two-dimensional material, and the lower face is permeable to fluids, wherein the at least one planar capillary membrane system is arranged in the interior of the pouch and is connected to at least one supply line, such that liquids, media, gases and/or other substances can be conveyed through the supply line and the at least one capillary membrane system, and wherein the at least one supply line is connectable to a supply unit or disposal unit outside the pouch-shaped wound dressing.

The wound dressing system is introduced into a wound to be treated in such a manner that the lower face of the pouch-shaped wound dressing rests on the wound. Through the at least one planar capillary membrane system, liquid can be fed to the wound, for example in the form of a nutrient solution, which liquid spreads in the pouch after discharge from the capillary membranes and is delivered to the wound through the semi-permeable lower face of the underside of the pouch. The capillary membrane system is then connected via the at least one supply line, e.g. via a pump, to a supply unit for the liquid, e.g. a reservoir for the nutrient solution.

The at least one capillary membrane system can also be used to suction exudate from the wound. In this case, the supply unit is a vacuum unit that is connected to the capillary membrane system by means of at least one supply line.

Supplying the wound with a liquid and suctioning the exudate from the wound can also be carried out intermittently via the at least one capillary membrane system by connecting the at least one supply line, for example via a T-piece, to a liquid reservoir via a first sub-line, and to a vacuum unit via a second sub-line. Liquids can be supplied or exudate can be suctioned off at predetermined time intervals by means of controllable shut-off valves.

In one embodiment, the capillary membranes of at least one capillary membrane system are designed to feed or discharge liquid media. In order to ensure uniform supply to the wound and removal from the wound, the capillary membranes are preferably characterized by high permeability to liquids. In this case, transmembrane flow of water in the capillary membranes preferably lies in the range of 0.01 to 50 mL/(min·cm²·bar).

In a further preferred embodiment, the wound dressing system comprises at least two planar capillary membrane systems, wherein one of the capillary membrane systems has capillary membranes suitable for gas transfer, e.g. membranes for oxygenation such as those disclosed in EP-A-1 144 096, EP-A-0 299 381 or DE-A-28 33 493. Oxygenation, i.e. supplying the wound being treated with oxygen, for example, can be carried out by means of such a capillary membrane system.

The at least one planar capillary membrane system is understood to be an arrangement consisting of at least one capillary membrane extending two-dimensionally in the interior of the pouch. The dimensions of the at least one planar capillary membrane system result from its external measurements in the two-dimensional extension. With regard to its two-dimensional extension, the at least one capillary membrane system preferably fills at least 20% and particularly preferably at least 50% of the two-dimensional extension of the interior of the pouch of the pouch-shaped wound dressing. With regard to its two-dimensional extension, it is particularly advantageous if the at least one capillary membrane system fills at least 70% of the two-dimensional extension of the interior of the pouch of the pouch-shaped wound dressing, wherein fill ratios in the range of 90% can also be achieved. It is advantageous if the planar capillary membrane system is arranged centrally in the pouch-shaped wound dressing.

Here, the at least one planar capillary membrane system consists of a single capillary membrane arranged in a meandering fashion in the interior of the pouch. In this embodiment, at least one of the ends of the meandering capillary membranes is open and connected to a supply line. However, the at least one capillary membrane system may also comprise a plurality of meandering capillary membranes which, together with their ends, open into a common supply line.

Naturally, the number of capillary membranes in the at least one planar capillary membrane system depends primarily on the size of the wound care system and thus on the size of the pouch-shaped wound dressing, which, in turn, must be adjusted to the size of the wound to be treated therewith. The at least one planar capillary membrane system can therefore be composed of about 10 to several hundred or thousand mutually parallel capillary membranes.

The mutually parallel capillary membranes are embedded at at least one of their ends in the wall at its outer periphery of the at least one supply line so as to be impermeable to fluids so that a fluid connection exists between the lumen of the supply line and the lumen of the capillary membranes and that liquids, media, gases and/or other substances can be conveyed through the supply line and the at least one capillary membrane system. The at least one supply line is preferably open at its one end and connectable to a supply unit or to a disposal unit, whereas the other end of the at least one supply line is closed. They can be embedded, for example, with a curable silicone material, a polyurethane or an epoxy resin. Curable silicone materials are preferably used because of their superior flexibility. If the capillary membranes are embedded in a supply line with only one of their ends, the other, opposite, end of the capillary membrane is closed by fusing or bonding, for example. The capillary membranes can also be open at both of their ends and embedded in a supply line with both of these two ends on one side of the arrangement, wherein the capillary membranes are then designed to be U-shaped at their free end and are thus closed there. In those cases, the capillary membranes are operated in the dead-end mode.

In particular with wider wound dressing systems, an embodiment of the at least one capillary membrane systems with mutually parallel capillary membranes is advantageous, in which the capillary membranes are open at both of their ends and embedded in a respective supply line, wherein the supply lines are then preferably located on opposite sides of the pouch-shaped wound dressing system. In this case, as well, embedding is carried out in such a way that the capillary membranes are embedded to be impermeable to fluid at the outer periphery and to create a fluid connection between the lumen of the respective supply line and the lumen of the capillary membranes. Such an embodiment with two supply lines makes supply and/or disposal possible in the cross-flow mode via the at least one capillary membrane system. With a view to good homogeneity of supply and/or disposal across the wound area, and in particular with wider mats or wound dressings, the design of the at least one capillary membrane system having two supply lines may be appropriate.

The diameter of the at least one supply line conforms primarily to the external diameter of the capillary membranes embedded in it. The at least one supply line therefore preferably has an internal diameter in the range of 0.1 to 10 mm. It is likewise preferred if the wall thickness ranges from 0.1 to 5 mm. In the event that a supply line having a non-circular cross-section is used, the equivalent diameter $d=4A/U$ of the internal cross-section is used as the internal diameter, where A is the area of the internal cross-section and U its circumference. For example, the internal cross-section of the supply line may also be oval, or approximately square or rectangular. For the at least one supply line, a silicone tube, for example, through the walls of which the capillary membranes pass and into which they are glued, has proven to be suitable. Preferably, the at least one common supply line is a flexible silicone tube.

Embedding or bonding in the wall of the supply line can be accomplished by means of conventional adhesives, such as, e.g., curable silicone materials, polyurethane resins or epoxy resins. In one embodiment of the wound dressing system, the connection of the at least one planar capillary membrane system with the at least one supply line can be arranged outside the pouch-shaped wound dressing on the upper face, and the at least one planar capillary membrane system for connection to the at least one supply line can exit from the pouch-shaped wound dressing via a through-opening that is impermeable to fluids. The through-opening can also be sealed, e.g., by means of a silicone material.

In a further embodiment of the wound dressing system, the connection of the at least one planar capillary membrane system with the at least one supply line can be located in the interior of the pouch and the at least one supply line can exit from the pouch-shaped wound dressing via a through-opening impermeable to fluids fitted to its external cross-section.

In an advantageous embodiment, the capillary membrane system may be designed in the form of a capillary membrane mat in which a plurality of mutually parallel capillary membranes are connected to one another by means of spaced and mutually parallel connection elements and are held at a distance from one another by the connection elements. In doing so, the connection elements can run transverse to the mutually parallel capillary membranes, or also at another angle. The connection elements can also be adhesive strips or, for example, strand-like elements made of a silicone material. In a preferred embodiment, the capillary membranes are connected by means of thread-like connection elements to form a mat. Particularly preferably, the connection elements are multifilament textile threads. Multifilament polyester threads, polypropylene threads or polytetrafluoroethylene threads have proven to be particularly successful multifilament textile threads.

In a preferred embodiment, the capillary membrane mat can be a knitted mat. In such knitted mats, the capillary membranes and the connecting fibers are knitted together, and the capillary membranes run transverse to the extension direction of the capillary membrane mat. The length of the capillary membranes is determined by the width of the mat. In a further preferred embodiment, the capillary membrane mat can be a woven mat. In such woven mats, the capillary membranes and the connecting fibers are woven together. The capillary membranes run in the extension direction or the running direction of the capillary membrane mat, and the textile fibers run transverse thereto. Capillary membrane knitted and woven mats, as well as ways of producing them, are described, for example, in DE 38 39 567, DE 43 08 850 and EP 0 442 147. Mats can be produced in a simple manner in particular by means of knitting technology, where the capillary membranes are designed in a U-shape at their free ends and closed off there. Such mats can be produced by depositing a meandering capillary membrane in mutually parallel strands, which are connected by the knitting fibers.

After the knitted mats have been completed, the U-shaped ends are severed on at least one side of the knitted mat, and the resulting open ends of the capillary membranes are then embedded in a supply line. In the event that the U-shaped ends are severed on both sides of the knitted mat, the resulting opposite open ends are embedded in respective supply lines.

In principle, all prior art organic polymers suitable for the formation of capillary membranes may be considered as materials for the capillary membranes, wherein said polymers must have good biocompatibility. Moreover, it is also required that the membrane polymer allows for sterilization of the wound dressing system, for example by steam sterilization, sterilization by γ-irradiation or sterilization by means of ethylene oxide. For this purpose, the organic polymers may be natural polymers or synthetically produced polymers. Natural polymers in particular are those based on cellulosic polymers, which likewise includes polymers that have been subjected to so-called polymer-analogous reactions. Examples of polymers based on cellulose are those from regenerated cellulose, cellulose acetate or modified cellulose, such as, e.g., cellulose esters, cellulose ethers, cellulose modified with benzyl groups (benzyl cellulose) or cellulose modified with dimethylaminoethyl or mixtures of these cellulosic polymers. Furthermore, polymers based on chitin or chitosan may also be used.

As synthetically produced polymers, i.e., synthetic polymers, those consisting of polyolefins, polyamides, polyacrylonitriles, polycarbonates, polyesters or sulfone polymers, and modifications, blends, mixtures or copolymers of these polymers obtained therefrom can be used. It is preferable to use those polymers based on sulfone polymers, such as, in particular, polysulfone or polyether sulfone. Further polymers may be admixed to the synthetic polymers as additives, such as, e.g., polyethylene oxide, polyhydroxy ether, polyethylene glycol, polyvinyl alcohol or polycaprolactone. In addition, the capillary membranes may also be coated with an additive. Such capillary membranes preferably contain a hydrophilizing agent, e.g., polyvinylpyrrolidone, or also hydrophilic modifications of these polymers.

The capillary membranes can be modified with a view to specific applications, e.g., via coupling of functional groups, or be coated, for example with heparin or one or more antibiotics.

The wound dressing system comprises a pouch-shaped wound dressing in the interior of the pouch of which is arranged the at least one capillary membrane system. The pouch-shaped wound dressing may have any contour. Preferably, however, the contour is round, oval, square or rectangular, and the lower and upper faces of the pouch-shaped wound dressing are connected at the outer margin or the outer edges of the wound dressing, for example by fusing or bonding. Cured silicone strips, among other things, are suitable for bonding. For rectangular or square pouch-shaped wound dressings, the planar capillary membrane system arranged therein preferably also has a rectangular or square contour. For round or oval pouch-like wound dressings, the at least one planar capillary membrane system contained therein is conveniently also designed to be square or rectangular, wherein, with regard to size, the previously specified dimensions apply. However, it may also be fitted to the contour of the pouch-shaped wound dressing, for example by suitably adapted end-fusing of the non-embedded ends of the capillary membranes in capillary membrane systems having only one supply line, resulting in an arched contour at this edge of the planar pouch-shaped wound dressing system.

As previously mentioned, the size of the pouch-shaped wound dressing naturally depends primarily on the size of the wound to be treated therewith. The size of the pouch-shaped wound dressing in its two-dimensional extension direction may be in the range of about 1 cm to about 1 m or more, in each case depending on the application.

The lower face of the pouch-shaped wound dressing is permeable to fluids. For this purpose, the lower face may consist, for example, of a nonwoven, two-dimensional material, a grid-like or web-like material, a perforated film or a semi-permeable microporous flat membrane. In an advantageous embodiment, the lower face consists of a nonwoven, two-dimensional material or a semi-permeable microporous flat membrane. The lower face preferably has a water permeability of at least 0.01 mL/(min·cm$^2$·bar) and particularly preferably at least 10 mL/(min·cm$^2$·bar). A lower face having a water permeability of at least 500 mL/(min·cm$^2$·bar) has been found to be most successful.

For applications of the wound dressing system in which the wound is not only provided with liquid via the wound dressing system, but in which disposal is carried out, i.e. a discharge of liquids from the wound and, in particular, a disposal of exudate, it is advantageous if the lower face has openings, the openings preferably having a diameter of at least 100 μm. For this purpose, openings having a diameter of no more than 10 mm are preferred and particularly preferred are those of no more than 5 mm. In the event that the lower face consists of a semi-permeable microporous flat membrane, in a preferred embodiment said membrane additionally has openings, e.g. in the form of perforations. In the event that the openings have a non-circular contour, the equivalent diameter D=4A/U of the opening is used as the diameter, where A is the area of the respective opening and U its circumference. The openings may be distributed regularly or irregularly over the surface of the lower face, wherein a regular, homogeneous distribution is preferred. The distance between the openings for this purpose may lie in the range of 1 to 20 mm, measured from the outer edge of the openings.

Lower and upper faces of the pouch-shaped wound dressing may consist of the same or different materials. However, whereas the lower face is always permeable to fluids, the upper face is preferably made of a preferably film-like material impermeable to fluids which is connected with the lower face at its side edge(s) so as to be impermeable to fluids. The upper face may also be a semi-permeable microporous flat membrane. In this case, however, the upper face has a lower permeability to fluids than the lower face, so that, when in use, the distribution of liquid fed to the lower face of the pouch-shaped wound dressing, and thus to the wound, is ensured. In the event that the lower and upper faces are the same or are made of semi-permeable microporous flat membranes of the same permeability, the lower face has perforations.

As materials for the lower or upper face of the pouch-shaped wound dressing, the same organic polymers which were specified earlier as polymers for the capillary membranes and which can be processed into flat films or flat membranes can in principle be considered. Preferably, the lower and/or the upper face of the pouch-shaped wound dressing are composed of polyolefins, polyamides, polyacrylonitriles, polycarbonates, polyesters or sulfone polymers, and modifications, blends, mixtures or copolymers of these polymers obtained therefrom. Particularly preferably the lower and upper faces comprise sulfone polymers, wherein polysulfone or polyether sulfone are most suitable.

The wound dressing system may also contain a plurality of capillary membrane systems in the pouch-shaped wound dressing which may be capable of assuming different tasks in the wound care system. Hence, the wound dressing system may have a first capillary membrane system with which the wound can be supplied with a nutrient solution, for example, and a second capillary membrane system with which the exudate can be removed from the wound. As previously explained, the wound dressing system may also comprise a capillary membrane system with which oxidation can be carried out, i.e., with which oxygen can be fed to the wound. The combination with another capillary membrane system is also possible, with which temperature control or pH regulation can be achieved, for example. The capillary membranes contained in the capillary membrane systems are adapted to the respective task of the capillary membrane system, as has already been explained above, wherein the capillary membranes of the individual systems may also differ with respect to the materials of which they are made. The systems may furthermore also be different with respect to their structure, for example, regarding the number of capillary membranes contained in them, their distance from one another, the number of supply lines to which they are connected, etc.

In this case, the respective capillary membrane systems can be superimposed on each other. However, it is also possible that two different capillary membrane systems are interconnected to form a mat, wherein the capillary membranes of the different capillary membrane systems are embedded with their ends in different supply lines, which are preferably arranged on opposite sides of the mat. Such mats can be obtained, for example, by knitting together offset meandering capillary membranes in which the U-shaped bends of the capillary membranes are located at different positions across the width of the mat. By cutting the respective outer U-shaped bends, the capillary membranes are opened on only one side of the mat and can be embedded in a supply line there.

In one embodiment, in particular in small wound dressings, exudate accumulating in the interior of the pouch can be removed through the upper face of the pouch-shaped wound dressing, e.g. by means of a suction hose attached to the upper face and be fluidically connected to the interior of the pouch. The suction hose can also be used in combination with a vacuum unit so as to create a vacuum inside the interior of the pouch when in use.

In one advantageous embodiment, a drainage system can be arranged in the interior of the pouch which is suitable for removing exudate from wounds being treated. As previously explained, the wound dressing system may have a separate capillary membrane system for removing exudate, which is a drainage system in this case. Moreover, the drainage system may preferably also be at least one drainage catheter which exits from the pouch-shaped wound dressing via a through-opening, fitted to its cross-section, and is connectable to a vacuum unit so as to create a vacuum inside the interior of the pouch when in use. The at least one drainage catheter can be a piece of tubing, for example of a silicone material, or a small tube which is arranged in the interior of the pouch of the wound dressing and which exits from the wound dressing via the through-opening. The segment of the at least one drainage catheter located in the interior of the wound dressing preferably has perforations in its wall, through which exudate, e.g., after connecting the at least one drainage catheter to a vacuum unit, can be suctioned from the wound or from the interior of the pouch-shaped wound dressing and from the wound. The at least one drainage catheter preferably has an internal diameter in the range of 0.1 to 15 mm and a wall thickness in the range of 0.1 to 3 mm and preferably extends across at least the entire length or width of the interior of the pouch. The drainage catheter can also have a non-circular cross-section. In that case, the equivalent diameter $d_D=4A_D/U_D$ of the internal cross-section is used as the internal diameter, where $A_D$ is the area of the internal cross-section of the drainage catheter and $U_D$ its circumference.

As explained, the at least one supply line of the at least one capillary membrane system can exit from the pouch-shaped wound dressing via a through-opening, fitted to its external cross-section to be impermeable to fluids and is connectable to a supply unit outside the pouch-shaped wound dressing. The same applies with respect to the optional drainage catheter which exits from the wound dressing via a through-opening fitted to the external cross-section of the drainage catheter. The through-opening can be located in the upper face of the pouch-shaped wound dressing or in the area of the connection between the lower and upper face of the wound dressing. In the case of through-openings that are arranged in the upper face of the wound dressing, it is necessary to seal, for example with silicone, the through-openings between the supply line or the drainage catheter and the sheet-like material forming the upper face. In the arrangement of the through-openings in the area of the connection between lower and upper face of the wound dressing, sealing can be accomplished simultaneously by fusing or bonding the lower and upper face. With respect to handling, it is appropriate if the supply lines and optional drainage lines exit from the pouch-shaped wound dressing to the same side of the wound dressing.

The characterization of the properties of the capillary membranes or flat membranes used in the wound dressing system is based on the following measurement methods:

Transmembrane Flow (Water Permeability) for Capillary Membranes:

A test cell with a defined capillary membrane number and length is produced from the capillary membranes to be tested. To that end, at their ends, the capillary membranes are embedded at both sides in a polyurethane resin. After the resin has cured, the embeddings are cut to a length of about 30 mm, the cut thus opening the lumens of the capillary membranes. The capillary lumens in the embeddings must be checked for permeability. The free length of the capillary membranes between the embeddings is typically 120+/−10 mm. The number of capillary membranes should be calculated such that a filtration area of 30 cm² is provided in the test cell, taking into account the free length and the internal diameter of the capillary membranes.

The test cell is integrated into a test apparatus and perfused with ultrafiltered and deionized water set to 25° C. at a defined test pressure (about 0.4 bar). The amount of filtered water obtained during a measuring time of 2 min., i.e., the permeate produced during the measurement, is gravimetrically or volumetrically determined. Before starting the measurement, air must be purged from the system. To determine the TMF, the test apparatus measures the inlet and outlet pressure at the test cell. The measurement is carried out at 25° C.

The transmembrane flow, TMF, is determined according to formula (I).

$$TMF = \frac{V_w}{\Delta t \cdot A_M \cdot \Delta p} \left[ \frac{\text{ml}}{\text{cm}^2 \cdot \text{min} \cdot \text{bar}} \right] \quad \text{(I)}$$

Where:

$V_w$=water volume [mL] perfused through the membrane sample during the measuring time $\Delta t$=measuring time [min]

$A_M$=perfused area of the membrane sample (typically 30 cm²)

$\Delta p$=pressure set during the measurement [bar]

Permeability to Water of the Lower Face of the Pouch-Shaped Wound Dressing:

Disk-shaped samples to be tested are punched out of the two-dimensional material of the lower face of the pouch-shaped wound dressing and clamped, impermeable to liquid, at the circumference in a suitable sample holder resulting in a free measuring area of 17.35 cm². The sample holder is located in a housing that can be perfused by pressurized water. The clamped sample is then perfused with deionized water set to 25° C. at a defined pressure of between 0.1 and 0.2 bar. The water volume perfused through the sample during a measuring time of 60 s is gravimetrically or volumetrically determined.

The permeability to water, $TMF_W$, is determined according to formula (II).

$$TMF_w = \frac{V_w}{\Delta t \cdot A_M \cdot \Delta p} \left[\frac{ml}{cm^2 \cdot min \cdot bar}\right] \quad (II)$$

Where:

$V_w$=water volume [mL] perfused through the sample during the measuring time $\Delta t$=measuring time [min]

$A_M$=perfused area of the sample (typically 17.35 cm²)

$\Delta p$=pressure set during the measurement [bar]

Figure 2:
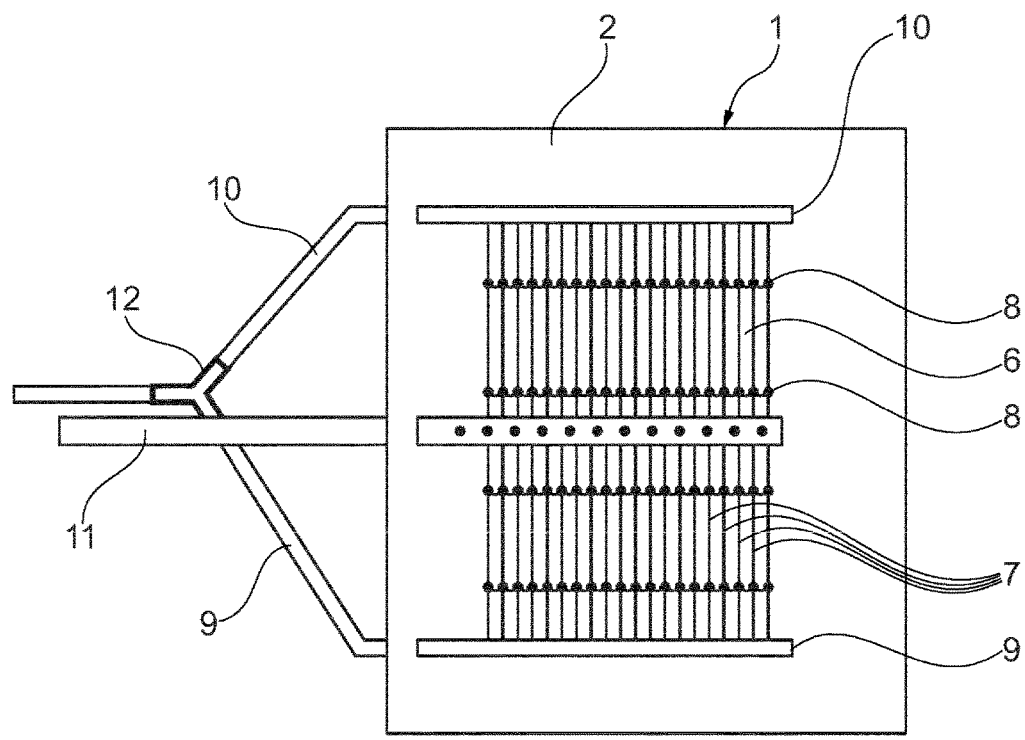

The invention is further explained by means of the following figures, wherein the scope of the invention is not limited by the figures:

The following is shown:

FIG. 1: a schematic view of a cross-section through a pouch-shaped wound dressing system according to the invention FIG. 2: in a section A-A, a cross-section of the wound dressing system depicted in FIG. 1

Figure 3:
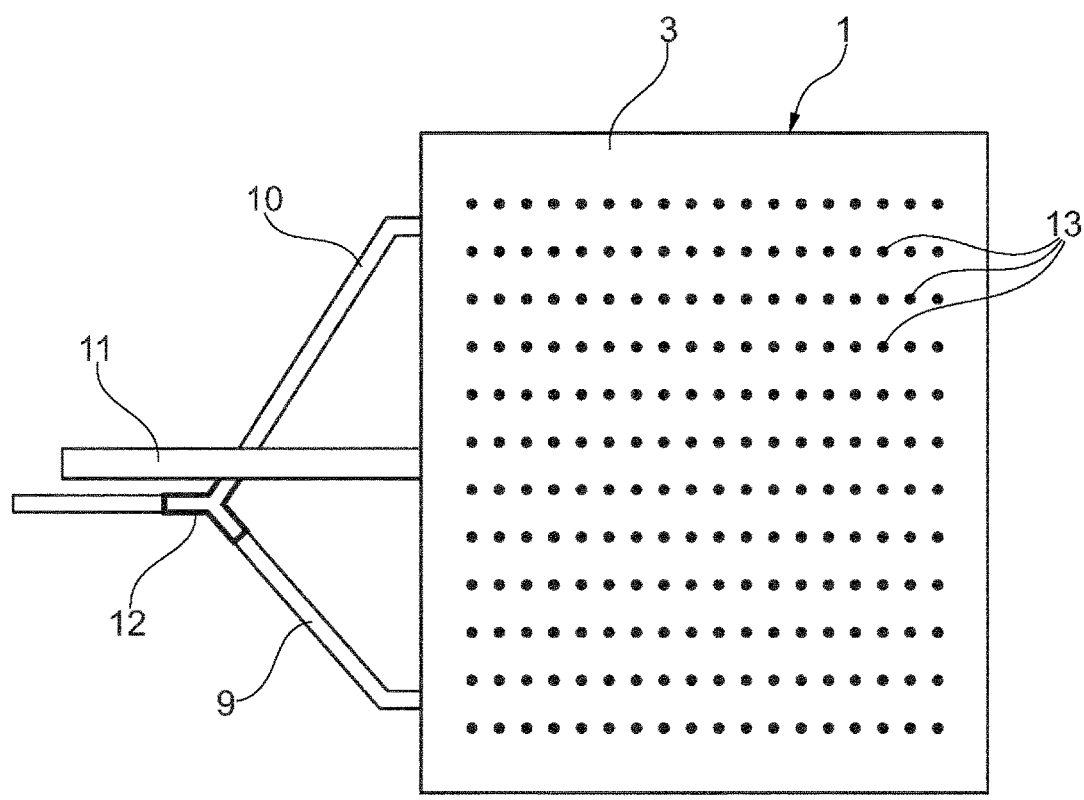

FIG. 3: the wound dressing system of FIGS. 1 and 2 in a plan view onto the bottom side of the lower face of the pouch-shaped wound dressing FIG. 1 shows a schematic view of a cross-section through a pouch-shaped wound dressing system with a pouch-shaped wound dressing 1 comprising an upper face 2 and a lower face 3 which are fused together, for example, at their edge 4a, 4b, thus creating a closed interior of the pouch 5. In the interior of the pouch 5, a planar capillary membrane system is arranged, comprising capillary membranes 7 which are interconnected and held at a distance from one another by mutually parallel connection elements 8, preferably in the form of multifilament threads.

In the present case, the opposite ends of the capillary membranes 7 open into supply lines 9, 10, so that liquids, media, gases and/or other substances can be conveyed through the supply lines 9, 10 and the capillary membrane system 6. The supply lines 9, 10 exit through the upper face 2 of the pouch-shaped wound dressing 1 (not shown here).

Below the planar capillary membrane systems 6, a drainage tube 11 is arranged, through which, e.g., exudate accumulating in the wound can be removed.

FIG. 2 shows a cross-section along the line A-A of the wound dressing system depicted in FIG. 1. This is in principle a plan view from a position below the lower face 3 of the pouch-shaped wound dressing 1 in the direction of the upper face 2 of the pouch-shaped wound dressing 1. Below the upper face 2, i.e. as shown in FIG. 1, between lower face 3 and upper face 2, the planar capillary membrane system 6 is arranged, which is composed of mutually parallel capillary membranes 7 which are interconnected and held at a distance from one another by the connection elements 8. The opposite ends of the capillary membranes 7 are embedded in the supply lines 9, 10, so that liquids, media, gases and/or other substances can be conveyed through the supply lines 9, 10 and the capillary membrane system 6. The supply lines 9, 10 exit from the pouch-shaped wound dressing 1 through the upper face 2 of the pouch-shaped wound dressing 1 through correspondingly fitted openings in the upper face 2 and, in the present example, are merged via a Y-connector 12 outside the pouch-shaped wound dressing 1. Hence, in the present case, the planar capillary membrane system 6 is operated in the dead-end mode, i.e. a medium fed via the supply lines 9, 10 is introduced into the capillary membrane system 6 and enters completely into the interior of the pouch through the walls of the capillary membranes 7.

FIG. 2 also depicts a drainage tube 11 arranged below the capillary membrane system 6. The wall of the drainage tube is perforated, so that, e.g., exudate accumulating in the wound can be suctioned off via the drainage tube and thus be removed from the wound. The drainage tube 11 also exits the pouch-shaped wound dressing 1 via a correspondingly fitted opening in the upper face 2 and is connectable, e.g., to a vacuum unit (not shown).

FIG. 3 shows the wound dressing system of FIGS. 1 and 2 in a plan view onto the bottom side of the lower face 3 of the pouch-shaped wound dressing. This bottom side of the lower face of the pouch-shaped wound dressing is placed on the wound when in use.

In the example illustrated, a lower face 3 is shown which has perforations 13 in its surface, wherein the perforations are uniformly distributed over the area and arranged in rows relative to one another. Other distributions of the perforation are also possible, of course. Nutrient solutions introduced into the interior of the pouch, for example, can be uniformly fed to the wound by means of the capillary membrane systems contained in the wound dressing through the perforations in the lower face of the pouch-shaped wound dressing. It is likewise possible to suction exudate from the wound via the perforations and thus remove exudate from the wound.

FIG. 3 also depicts the supply lines 9, 10, which exit from the (not shown) upper face of the pouch-shaped wound dressing 1 and are merged outside the pouch-shaped wound dressing via a Y-connector 12. Likewise depicted is the drainage tube 11, via which exudate accumulating in the wound, e.g., can be removed and which, like the supply lines 9, 10, exist the upper face of the pouch-shaped wound dressing 1, as shown in FIG. 1.

The invention claimed is:

1. A wound dressing system for introducing into a wound, comprising at least one planar capillary membrane system, the at least one planar capillary membrane system is arranged in a pouch-shaped wound dressing, which is closed at its outer edge and which has an upper face, a lower face and an interior of the pouch-shaped wound dressing,
    wherein the lower face and the upper face are each formed from a two-dimensional material, and the lower face is permeable to fluids, wherein the lower face and the upper face are connected at the outer edge by fusing or bonding, and wherein the at least one planar capillary membrane system comprises a lumen and is arranged in the interior of the pouch-shaped wound dressing and is connected to at least one supply line, such that liquids, media, gases and/or other substances can be conveyed through the supply line and the lumen of the at least one planar capillary membrane system; and wherein the at least one planar capillary membrane system is designed in the form of a mat of mutually parallel capillary membranes and lumens, wherein the capillary membranes and lumens in the mat are connected to one another by spaced and mutually parallel connection elements and are held at a distance from one another by the connection elements.

2. The pouch-shaped wound dressing system according to claim 1, characterized in that the lower face of the pouch-shaped wound dressing is formed from a nonwoven, two-dimensional material or a semi-permeable microporous flat membrane.

3. The pouch-shaped wound dressing system according to claim 2, characterized in that the lower face of the pouch-shaped wound dressing is formed from the semi-permeable microporous flat membrane.

4. The pouch-shaped wound dressing system according to claim 1, characterized in that the lower face of the pouch-shaped wound dressing has a water permeability of at least 0.01 mL/(min·cm²·bar).

5. The pouch-shaped wound dressing system according to claim 1, characterized in that the lower face of the pouch-shaped wound dressing has openings.

6. The pouch-shaped wound dressing system according to claim 1, characterized in that the connection of the at least one planar capillary membrane system with the at least one supply line can be located in the interior of the pouch and the at least one supply line exits from the pouch-shaped wound dressing via a through-opening fitted to its external cross-section so as to be impermeable to fluids.

7. The pouch-shaped wound dressing system according to claim 1, characterized in that the connection of the at least one planar capillary membrane system with the at least one supply line is arranged on the upper face outside the pouch-shaped wound dressing, and the at least one planar capillary membrane system for connection to the at least one supply line exits from the pouch-shaped wound dressing via a through-opening fitted to be impermeable to fluids.

8. The pouch-shaped wound dressing system according to claim 1, characterized in that a drainage system is arranged in the interior of the pouch-shaped wound dressing system which is suitable for removing exudate from wounds to be treated.

9. The pouch-shaped wound dressing system according to claim 8, characterized in that the drainage system is a drainage catheter which exits from the pouch-shaped wound dressing via a through-opening fitted to its cross-section to be impermeable to fluids.

10. The pouch-shaped wound dressing system according to claim 1, characterized in that the at least one planar capillary membrane system are embedded with at least one of their ends in the at least one supply line.

11. The pouch-shaped wound dressing system according to claim 1, characterized in that the at least one planar capillary membrane system is connected to two supply lines, wherein the capillary membranes and lumens are embedded with their opposite ends in a respective supply line.

12. The pouch-shaped wound dressing system according to claim 1, characterized in that the at least one capillary membrane system has a transmembrane flow for water in the range of 0.01 to 50 mL/(min·cm²·bar).

* * * * *